(12) United States Patent  
Crawford

(10) Patent No.: US 7,510,722 B2  
(45) Date of Patent: Mar. 31, 2009

(54) APPARATUS FOR DISPENSING A BIRD HAZE PRODUCT FROM A CAN

(76) Inventor: Gary Crawford, 2100 196th St. SW., #138, Lynnwood, WA (US) 98036

( * ) Notice: Subject to any disclaimer, the term of this patent is extended or adjusted under 35 U.S.C. 154(b) by 0 days.

(21) Appl. No.: 10/908,323

(22) Filed: May 6, 2005

(65) Prior Publication Data

US 2006/0251691 A1    Nov. 9, 2006

(51) Int. Cl.  
*A01N 25/06* (2006.01)
(52) U.S. Cl. .......... 424/405; 424/45; 514/535; 514/536; 514/537; 514/538; 514/920
(58) Field of Classification Search .......... None  
See application file for complete search history.

(56) References Cited

U.S. PATENT DOCUMENTS

| | | | | |
|---|---|---|---|---|
| 3,159,535 A | * | 12/1964 | Sesso et al. ............ | 424/45 |
| 5,145,604 A | * | 9/1992 | Neumiller ............ | 516/71 |
| 5,296,226 A | * | 3/1994 | Askham ............ | 424/405 |
| 5,792,465 A | * | 8/1998 | Hagarty ............ | 424/405 |
| 6,689,397 B2 | | 2/2004 | Clark et al. | |
| 7,334,745 B2 | | 2/2008 | Crawford | |

OTHER PUBLICATIONS

Casida- Pyrethrum- pp. 267-274, 1973.*  
Seymour The New Garden Encyclopedia -pp. 1161-1166, 1941.*  
U.Delaware—Pesticide Applicator—Training Manual, pp. 6-1, 6-3 to 6-7. 1990.*

* cited by examiner

*Primary Examiner*—Neil Levy  
(74) *Attorney, Agent, or Firm*—Black Lowe & Graham PLLC

(57) ABSTRACT

An aerosol tiny mist hazer apparatus. The apparatus has an aerosol can that contains about 10% by weight Methyl Anthranilate oil and about 90% by weight of an isobutane and propane propellant mixture. The apparatus has an aerosol valve with a vapor tap at the top and having a fine aerosol nozzle for producing a fine, evenly dispersed and stable haze having particle sizes less than 20 microns (in the form of a breathable haze) for use in maintaining birds flying away.

17 Claims, 2 Drawing Sheets

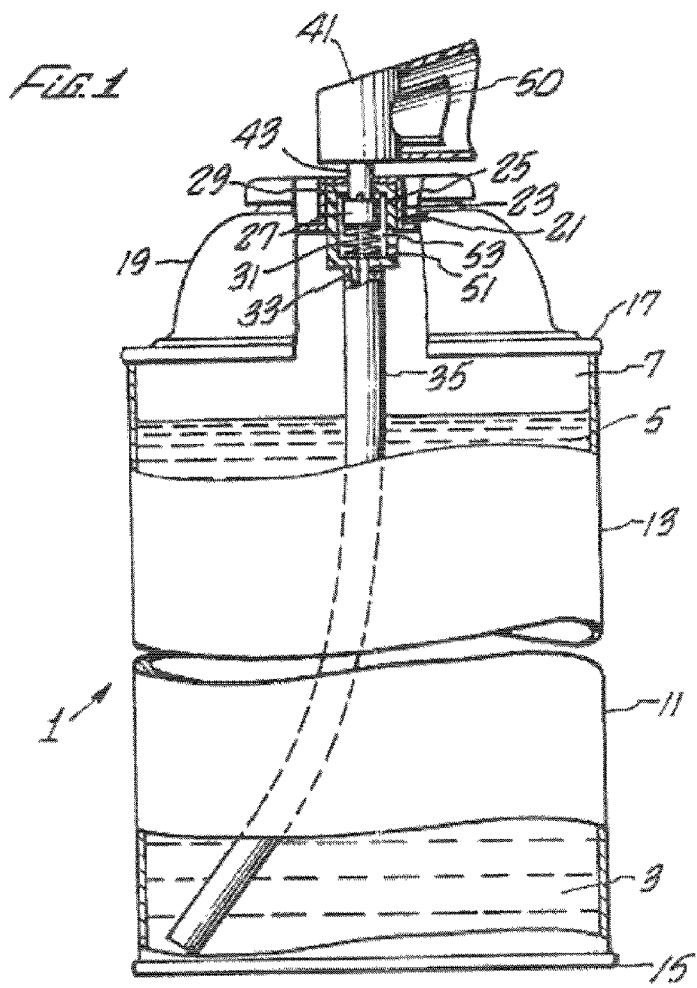
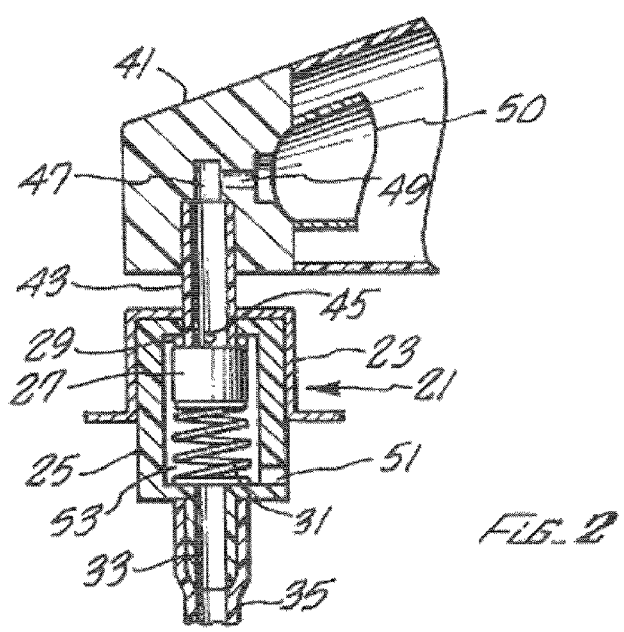

```
         ┌──────────────┐ 63
         │   AGITATE    │
         └──────┬───────┘
                ▼
         ┌──────────────┐ 65
         │ MIX PROPELLANT│
         │   AND OIL    │
         └──────┬───────┘
                ▼
         ┌──────────────┐ 67
         │ POINT NEEDLE │
         └──────┬───────┘
                ▼
         ┌──────────────┐ 71
         │ PRESS PLUNGER│
         └──────┬───────┘
                ▼
         ┌──────────────┐ 73
         │   LIFT OIL-  │
         │  PROPELLANT  │
         └──────┬───────┘
                ▼
         ┌──────────────┐ 75
         │  MIX VAPOR   │
         └──────┬───────┘
                ▼
         ┌──────────────┐ 77
         │ABRUPTLY REDUCE│
         │   PRESSURE   │
         └──────┬───────┘
                ▼
         ┌──────────────┐ 79
         │DISPENSE MICRON│
         │  PARTICLES   │
         └──────┬───────┘
                ▼
         ┌──────────────┐ 81
         │AWAIT MOMENTARY│
         │  DISPERSION  │
         └──────┬───────┘
                ▼
         ┌──────────────┐ 83
         │BIRDS FLY INTO│
         │HAZE DISPERSION│
         └──────────────┘
```

APPARATUS FOR DISPENSING A BIRD HAZE PRODUCT FROM A CAN

BACKGROUND OF THE INVENTION

Agriculture and food storage facilities face a problem when wishing to guard an area against constant roosting of birds, due to the droppings causing a health concern. When the birds roost in high areas, their droppings from overhead in areas that are supposed to be clean from dirt or debris, cause health and contamination concerns. For years, Methyl Anthranilate has been used as a deterrent for birds to induce them to leave a given area through the use of using heated fog machines or spraying the chemical on the food itself the birds would eat. This chemical, Methyl Anthranilate (MA), is avian specific and has been used worldwide for deterring birds.

Some machines used to distribute the chemical MA in the past needed advance preparation, heat up time, and an operator to distribute the heavy fog, delaying operations or requiring additional time. To cause a reaction in the birds, it is also necessary that the smoke not be too visible. When birds see the dense smoke created by these heated fog machines, it causes them to act defensively by protecting themselves and not actually breathing during the release of the chemical. This chemical is harmless to birds, animals and people, but causes a reaction internally only in birds, making them cough. Birds find this irritation substantial enough to want to leave the area, without having any after effects other than the memory of not liking the feeling in that area. Due to the good memory of birds, they remember they did not like it and stay away after 2 or 3 exposures.

A chemical was added to the pure form of Methyl Anthranilate as a carrier that was food grade inert ingredient mixed well with the active ingredient at 14.5%-41%. The existing machine with heated coils that burned the fluid created a fog application that would repel the birds by simply having the birds breathe the fog, but the odor created from the heating process was offensive to people and animals also. This application was only to cause birds to leave the area, not to kill them. After several applications of the fog or clouds of chemicals where the birds nested, the birds would leave, not liking the smell and effect it had on the birds throat.

When fogging with the chemical ReJeX-it®TP-40 in enclosed confines of a hangar or warehouse, 1-4 oz per 10,000 cu ft. gave excellent results. It was found that it is not necessary to operate the heated fogger at its highest capacity. Most of the time better results were obtained at less than 50% of the design rate to generate smaller more efficient particles or droplets. Operation of the Curtis Dyna-Fogger at very low output was still a very high output, due to this machine being designed for high output and not designed for very low output. The droplet size under 20 microns would be less than 10%, causing the psychological conclusion that more fog was needed to obtain the effects necessary to make a reaction with the birds effective. When 80% of the fog generated was ineffective, it also was a waste of chemical and caused a terrible odor when heated.

Other discoveries were made concerning the heating of the fluid. This heat process would sometimes reduce the effectiveness of the product, causing a less than desired result. A mechanical unit utilizing a compressor to compress the fluid to create a spray or mist under high pressure was a product called Universal Mist. It was applied in several locations because the manufacturer was claiming the particles to be smaller than 20 microns when the fluid was pressurized at 800 psi and forced through an orifice the size of 0.008. CITC sells a similar product and found testing to show the particles to be much larger (over 30 microns). The majority of particles (95%) were larger than the required 20 micron size and the overspray of the chemical caused damage to plants and paint on buildings. Damage was extensive and expensive for the replacement. Since there was not sufficient amount of smaller particles in the mist, it was abandoned after repairs had to be made that were too costly. The large and heavy weight of the particles caused the particles to stay low to the ground, causing a residue build-up that made a large impact on the plants and paint. Disadvantages of spraying the chemical Methyl Anthranilate when used in its' current applications on fruits and berries is considerable, limiting it to reduced performance. MA breaks down into anthracitic acid and causes severe phytotoxicity on leaves of treated plants when in large amounts of large size droplets. Second, it is a volatile compound and has a short residual on exposed fruit. Third, to repel birds, a large amount must be consumed in one bite to be effective. It is less effective when applied uniformly on plants by spraying.

PMC specialties Co. in Cincinnati developed a formulation that did not cause phytotoxicity. They encapsulated the MA in clay particles, so the chemical that is sprayed on the fruits and berries was release slowly over time when sprayed onto the plants. This would stay on the plants for a longer period, giving them a messy solution.

Methyl Anthranilate used in Rejex-It was disappointing when applying the fluid in a heavy spray or mist. Another chemical fluid mix using MA is a company in Washington called Bird Shield is now formulated to not cause leaf burn from the high phytotoxicity. But according to Rutgers cooperative Extension at New Jersey Agriculture Experiment Station on Jul. 16, 1996, both formulations were disappointing. Although some deterrence was noted within 3 days of application, the effect was not long lasting. Similar results have been reported from Oregon, Florida and Michigan. In spite of these disappointing results, Bird Shield was labeled as authorized for use in 1996 on blueberries.

Applications of the chemical on plants over time results in the flavor/odor of the chemical MA become into the taste of the grapes and blueberries. This was unacceptable in large amounts being sprayed over fields. In small amounts, it was not that effective in prohibiting birds from feeding. So the dilemma of what can be effective for the birds and not effect the plant or fruit is posed.

Other bird abatement methods included scarecrows, flashy metal, tinsel, loud noise, irritating noise, dogs, netting, thick emulsions causing stickiness on the claws, etc. But none were enough to cause the birds to stay away long enough to be called a total success or clean enough that the method did not cause a visual sightly mess. The birds seemed to outsmart these devices after just a few weeks and it became ineffective or it was too difficult to clean up.

Even though the mechanical breakdown with a propellant is common (referred to as aerosol mist), all other mechanical compressed air methods did not have the technology of using the vapor tap effect combined with the mix of propellant inside a canister with the chemical MA under pressure to release to a fine orifice to cause the breakdown of the chemical fluid to be so small (below 20 microns).

A need exists for a tiny portable or handheld mist hazer for dispersing the chemical known as Methyl Anthranilate in a mixture that produces a very tiny particle size without the need for using heat as the method of reducing the size, which is highly mobile, portable and quick and easy to use. That need has persisted without solution over a long time. This invention prefers using small particle amounts of Methyl Anthranilate (MA) through the use of non-heated, pressurized chemical and mix of the chemical with the vapor to form smaller particles of smoke, haze or mist when trying to protect areas from birds through the use of smoke, haze or mist without the use of heating (bad odor) and reducing the size of the particle to be smaller than the heated type smoke generator applicator.

Efforts to keep birds out of a given area for cleanliness by using a transparent haze with very small particles or when trying to clear the area of birds above an area that is designated to be clean, can now be pleasant to people, animals and other inhabitants without the use of heating the chemical. Heated foggers caused more problems than solved them. While machines are available which produce smoke, haze or mist, the machines are bulky and difficult to transport and relocate and often require personnel specifically assigned for their operation, as well as the chemical reacts to the heat that is used to form a fog, smoke or haze that has a very distasteful odor.

BRIEF SUMMARY OF THE INVENTION

The present invention solves the problems of breaking 80% of the particle size at breathing levels acceptable to birds, without the use of heat to create an avian specific remedy to entice birds to stay away or leave the given area when flying in or out. Now this combined solution can be placed inside a portable canister for the bird industry. It has been introduced with several changes to modify its ability to perform with the chemicals associated with bird repelling effects. The application of a transparent small particle haze instead of a thick fog from heating chemicals is considerably different and specific instructions show major changes in its application process.

The current invention utilizes the concept that MA broken down into particles smaller than 20 microns, will be at breathing level of birds and cause an irritation when they are flying into the haze that urges them to leave the area. The preferred operation of a mechanical compressed propellant gas is mixed by being in the liquid state and located at the bottom of the canister, mixing with the chemical MA, which is then released when the nozzles is depressed, forcing the mixture through a fine orifice for vaporization of particles below 20 micron. The canister must be able to distribute the haze product of bird repellant in its haze form by quietly penetrating the nesting or brooding area. Only the small particles are needed, the haze being released to instantly be further separated by air or air movement or fans outside of the canister to keep the small particles from reuniting or coagulating to form larger particle sizes. The use of tubes connected to the outside of the nozzle is not preferred, but detrimental to the goal of getting as many small particles apart as quickly as possible.

When the smaller particle is at or below 20 microns, an irritation will occur, causing the bird to cough even more. A cough can only happen inside the birds nasal passage if it is able to fully inhale the chemical so that it penetrates deeper into the nasal passage of the bird. We are utilizing Dr. Vogt's theory of "birds having a very good memory," posted in 1997. This coughing causes the bird to remember the event at that specific location and not want to come back to the same area. The fluid must be vaporized small enough to float freely about and be able to penetrate secretly into the nasal passage of the bird without the bird visually being able to see the particles in the air or hear a sound of a loud fogger that would signal their defense mechanism.

The present invention provides a hand-held portable aerosol tiny mist hazer which uses minute suspensions of Methyl Anthranilate oil and a liquefied gaseous propellant which are dispensed under an abrupt pressure change while being mixed with separate vapors of the propellant to produce a fine, evenly dispersed and stable haze having particle sizes less than 20 microns. After a few moments to allow for uniform dispersion, the haze appears as smoke, mist or haze and causes birds that fly through the hazed area to be irritated enough to leave due to the avian specific reaction of the finer particle inside their breathing chamber. This occurs only when they fly and breathe more rapidly.

An aerosol tiny mist hazer apparatus has an aerosol can containing about 10% by weight Methyl Anthranilate oil and about 90% by weight of an isobutane and propane propellant mixture and having an aerosol valve with a vapor tap located at the top of the inside chamber of the canister into the feeding tube connected to and having a fine aerosol nozzle for producing a fine, evenly dispersed and stable haze having particle sizes less than 20 microns.

A preferred tiny mist haze producing mixture has about 5-20% Methyl Anthranilate oil and about 80-95% of a hydrocarbon propellant for dispensing from a can under the vaporization pressure of the propellant.

In the preferred product the hydrocarbon propellant comprises a mixture of liquid isobutane and propane that mixes with the chemical MA when under pressure inside the canister and located at the bottom of the can.

Preferably the Methyl Anthranilate oil may also be mixed with a white food grade mineral oil but will work when mixed with soy bean oil or other oil based carriers of food grade quality.

A preferred oil is a light white food grade mineral oil comprising a homogeneous mixture of aliphatic and alicyclic hydrocarbons.

The preferred method of creating a tiny mist haze over a general area where birds migrate or propel themselves by flying through the area is with the mixture of MA oil in a liquid hydrocarbon propellant under pressure and dispensing the mixture of chemicals and liquid propellant through a fine aerosol nozzle and producing particles having a size less than 20 microns.

The propellant instantly changes to air from its liquid state as the pressure component of the canister. When under pressure, the propellant then is in two states, liquid and air with liquid at the bottom and air at the top. As the propellant is released out of the orifice, the combination of liquid propellant and air propellant are both released simultaneously. As the liquid propellant is released, it also becomes a vapor.

In the preferred method, the mixing further includes releasing a vapor of the propellant through the aerosol nozzle concurrently with the release of the intimate dispersion of the propellant and the Methyl Anthranilate oil creating yet another breakdown in size of particles below 15 microns to as low as 5 micron size particles.

The intimately mixed dispersion of the Methyl Anthranilate oil and the hydrocarbon propellant is pumped through a long tube extending to the bottom of an aerosol container wherein the mixture of chemicals and the Methyl Anthranilate oil are also mixed with the liquid from the propellant when it is under pressure of 85 psi or more. Concurrently vapors of the hydrocarbon propellant located at the top of the canister flow through a vapor tap located also at the top of the canister and away from this mixture of liquid at the bottom of the inside of the canister. The vapor and intimate mixture rapidly decompress and atomize into micron particles in a fine nozzle to be released quickly into an open area. As soon as the particles are released, air movement to scatter the particles form an even, transparent haze that is not visible unless well lit.

After releasing the micron particles in the atmosphere and allowing the resultant haze to stabilize, birds that fly through the haze will become more likely to breathe the smaller particle, irritating their bronchial tubes and causing them to leave the area. After releasing the micron particles in the atmosphere and allowing the haze to stabilize, birds that fly through the haze, are irritated, not harmed, and leave, not wanting to return. As a result, the droppings from birds are no longer a health concern due to the birds not wanting to be next to or inside the area where they have inhaled this irritant. These and further and other objects and features of the invention are apparent in the disclosure which includes the above and ongoing description, including the claims and the drawings.

BRIEF DESCRIPTION OF THE SEVERAL VIEWS OF THE DRAWING

The preferred and alternative embodiments of the present invention are described in detail below with reference to the following drawings.

FIG. 1 is a view partially in cross section of an aerosol tiny mist hazer of the present invention;

FIG. 2 is a detail of one form of a valve. Other valves contain a locking mechanism that can be used to sustain long periods of release without holding the release button in the release position; and FIG. 3 is a flow chart of steps of the present invention.

DETAILED DESCRIPTION OF THE INVENTION

Referring to FIG. 1 a tiny mist hazer canister of the present invention is generally indicated by the numeral 1. The hazer 1 has contents of about 10% Methyl Anthranilate oil 3 and about 90% of a propellant mixture 5 of isobutane and propane. The relative percentages of the fluids remain substantially constant during depletion of contents of the can by virtue of the substantially constant composition of the exhaust from the can. While less propellant can be used effectively, it is desirable to have an excess of the propellant in the can. The excess propellant ensures that the haze will be delivered under the pressure differential necessary to produce a fine particle size and to project the particles an appreciable distance from the nozzle, so as to mix with the air and separate as far as possible.

The excess propellant and excess pressure is highly desired so that the particles are sufficiently projected for dispersion so as not to agglomerate or coagulate and so that all of the oil is dispersed under sufficient pressure to ensure atomization of the oil particles to less than 20 microns in size so that the oil particles do not gather on adjacent surfaces or collect on horizontal surfaces. Many of the particles may be under 15 micron, under 10 micron, and under 5 micron.

Any suitable Methyl Anthranilate oil may be used. Preferably the mix would be with a mineral oil as a food grade mineral oil which is suitable for use on food contact surfaces and food processors which require lubrication or with a soy bean oil for food related items. Preferably the oil is a homogeneous mixture of complete aliphatic and alicyclic hydrocarbons. One suitable source of white mineral oil markets its product under the trademark RUDOL. A Methyl Anthranilate product under the trademark Fog Force is also available under the patent from Becker Underwood.

A preferred propellant is a mixture of isobutane and propane, preferably in equal parts. Such propellants are widely used as aerosol propellants. Examples of propellants are available under the trademark A-55 or M-55.

A 10% solution of the mixture of Methyl Anthranilate and oil in the propellant is preferred. 5-20% solutions or mixtures may be used. Too little mix wastes propellant. Too much mix wastes the mix of chemicals. Too much mix renders incorrect particle size or incorrect particle projection or both upon near exhaustion of the propellant.

The MA oil may be dissolved in the propellant or the oil may form a dispersion or suspension in the propellant. Preferably the container is agitated before exhausting the propellant and oil. Instructions are given to shake before use to insure smallest particle size.

Volume 7 above the surface of propellant 5 contains vaporized propellant. The vapor pressure provides the dispensing force of which the liquid propellant continually converts to as the vapor is used. The liquid propellant will immediately convert to vapor upon release of pressure inside the canister.

Aerosol container 11 has a side wall 13 and a bottom wall 15. A top wall 17 has edges joined to an upper edge of the side wall 13. A dome-shaped central portion 19 contains the aerosol valve 21. The aerosol valve 21 is shown in a schematic embodiment in which an outer wall 23 holds the valve 21. An inner cylinder 25 receives a piston 27, which is forced upward against an 0-ring seal which has to be made of non-reactive material 29 by spring 31. A nipple 33 on the lower end of the cylinder 25 receives an upper end of a tube 35. The lower end of the tube 35 has an opening which is positioned near an intersection of the side wall 13 and bottom wall 15 of the container 11. Pushing down on plunger 41 moves hollow shaft 43 downward unseating the piston 27 from the 0-ring 29. That allows fluid to flow under pressure through radial opening 45 into the hollow shaft 43, increasing with vapor from the vapor tap, into the vestibule 47 and out through the fine nozzle opening 49 as a fine mist. Mechanical breakup or swirl devices 50 swirl and deflect and break up the fine mist combined with the vapor from the propellant flowing from the nozzle.

In a preferred form of the invention cylinder 25 is provided with a vapor tap 51. Propellant vapor flows into chamber 53 through vapor tap 51. When push button 41 is depressed and hole 45 is communicated with chamber 53, vapor pressure of the propellant drives mixed propellant and oil upward through tube 35 and nipple 33 into chamber 53, where it mixes with vapor entering through port 51 before exiting 45 into the push button shaft 43, the vestibule 47 and outwardly with an abrupt pressure drop through nozzle 49. The tiny mist haze is stable. After a few moments with air movement allows uniform dispersion, the haze is ready for birds that may enter the area to fly through it and breathe the small particles, causing them to want to leave the area.

As shown in FIG. 3, an example process 61 includes at a block 63 agitating the can and at a block 65 mixing the propellant and oil into an intimate dispersion when the contents of the can are under pressure (80 psi or more). At a block 67, the nozzle is pointed. The steps at blocks 63 and 65 occur simultaneously. At a block 71, the plunger is pressed, which at block 73 lifts the oil propellant dispersion, at block 75 mixes the dispersion with vapor in the can and at a block 77 abruptly reduces pressure in the nozzle. At block 79, micron particles dispensed from the nozzle. The steps at blocks 71-79 take place concurrently and substantially simultaneously, while swirling the fine particles to cause them to separate as far away from the nozzle as possible before air movement separates them even more.

At block 81, one awaits momentary dispersion, which takes a minute. Existing air movement or air as moved with assistance of a fan spreads the particles apart for an evenly dispersed haze. At block 83, birds experience the haze haze 83. The entire process from the time that the can is first agitated and pointed takes for example about three minutes before haze is evenly spread inside an enclosed area. The micron particles remain dispersed and the tiny mist haze remains in place for a long period of time (up to 30 minutes if not exhausted) and may easily be replenished or renewed.

The tiny particle haze produced by the invention has a better effect and a light grape like odor than a Methyl Anthranilate Fogger, and without the side effects of a very heavy odor that is non-pleasant. While the invention has been described with reference to specific embodiments, modifications and variations may be made without departing from the scope of the invention as defined in the following claims.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A bird repellant aerosol haze system, comprising:
   an aerosol can;
   a pressurized bird repellant solution of about 10% by weight Methyl Anthranilate oil and about 90% by weight of at least one of an isobutane and propane propellant residing in the aerosol can, the Methyl Anthranilate oil comprising about 40% Methyl Anthranilate (MA) and about 60% oil;
   a gas of at least a pressure of 85 psi residing in the aerosol can;
   an aerosol valve coupled to the aerosol can; and
   an aerosol nozzle coupled to the valve, the aerosol nozzle operable to produce from the bird repellant solution a bird repellant vapor haze defined by an average particle size less than about 10 microns upon activation of the aerosol nozzle,
   wherein the vapor haze produced from the aerosol nozzle is not visible to a bird flying through the vapor haze.

2. The system of claim 1, further comprising a tube in fluid communication with the bird repellant solution, wherein the aerosol valve includes:
   a plunger chamber coupled at a first opening to the tube and having a vapor tap opening,
   wherein the plunger chamber causes received vapor of the propellant to be mixed with a liquid combination of the Methyl Anthranilate oil and a liquid portion of the propellant that is received from the tube, thereby causing the particle size released through the nozzle to have the average particle size of less than 10 microns.

3. The system of claim 2, wherein the Methyl Anthranilate oil is a mixture of 41% active Methyl Anthranilate (MA) and 59% of an oil compound.

4. The system of claim 3, wherein the oil compound is one of mineral or soy oil.

5. The system of claim 4, wherein the pressure in the pressurized can causes a portion of the propellant to liquefy such that the mixture of MA and mineral oil or soy oil mixes with the propellant liquid portion and wherein a portion of the propellant is in a gas state in the pressurized aerosol can.

6. The system of claim 5, wherein the mixture of MA, mineral oil or soy oil and the propellant liquid portion mixes again with the propellant gas portion such that a vapor is produced by the vapor tap away from the fluid located at the bottom of the canister while being released.

7. A bird repellant aerosol vapor haze system, comprising:
   a handheld portable aerosol can;
   a bird repellant comprising about 10% by weight Methyl Anthranilate oil and about 90% by weight of at least one of an isobutane and propane propellant, the Methyl Anthranilate oil comprising about 40% Methyl Anthranilate (MA) and about 60% oil, and wherein the Methyl Anthranilate oil and a liquid portion of the propellant is mixed when pressurized at a pressure of at least 85 psi;
   an aerosol valve coupled to the aerosol can; and
   an aerosol nozzle coupled to the aerosol valve, the aerosol nozzle operable to produce a bird repellant vapor haze when activated, the bird repellant vapor haze having an average particle size less than about 10 microns while being released.

8. The system of claim 7, a plunger chamber coupled at a first opening to the tube and having a vapor tap opening,
   wherein the plunger chamber causes received vapor of the propellant to be mixed with a liquid combination of the Methyl Anthranilate oil and propellant liquid portion that is received from the tube, thereby causing the particle size released through the nozzle to have an average particle size of less than 10 microns.

9. The system of claim 8, wherein the Methyl Anthranilate oil mix includes about 41% active Methyl Anthranilate (MA) and about 59% of an oil.

10. The system of claim 9, wherein the oil is one of mineral or soy oil.

11. The system of claim 10, wherein the mineral oil includes a white food grade mineral oil.

12. The system of claim 10, wherein the aerosol can is pressurized causing the Methyl Anthranilate oil to mix with the liquid portion of the propellant.

13. The system of claim 12, wherein the mixture of the Methyl Anthranilate oil and the liquid portion of the propellant communicate up the tube to mix again with vapor of the propellant.

14. The system of claim 13, wherein the propellant is at least one of isobutene and propane, and the Methyl Anthranilate oil and the at least one of isobutene and propane propellant mix when pressurized at approximately 95 psi causing the particle size released through the aerosol nozzle having an average particle size of about less than 5 microns.

15. The system of claim 1, wherein the vapor haze defined by the average particle size less than about 10 microns is configured to be inhaled by the flying bird deeply into its nasal passage.

16. The system of claim 7, wherein the vapor haze defined by the average particle size less than about 10 microns is configured to be inhaled by a flying bird deeply into its nasal passage.

17. The system of claim 7, wherein the vapor haze is invisible to a bird flying through the vapor haze.

* * * * *